United States Patent
Zhdanov

(10) Patent No.: US 10,242,126 B2
(45) Date of Patent: Mar. 26, 2019

(54) METHOD OF SIMULTANEOUS IMAGING OF DIFFERENT PHYSICAL PROPERTIES USING JOINT INVERSION OF MULTIPLE DATASETS

(71) Applicant: TechnoImaging, LLC, Salt Lake City, UT (US)

(72) Inventor: Michael S. Zhdanov, Holladay, UT (US)

(73) Assignee: TECHNOIMAGING, LLC, Salt Lake City, UT (US)

( * ) Notice: Subject to any disclaimer, the term of this patent is extended or adjusted under 35 U.S.C. 154(b) by 665 days.

(21) Appl. No.: 13/735,883

(22) Filed: Jan. 7, 2013

(65) Prior Publication Data

US 2013/0179130 A1 Jul. 11, 2013

Related U.S. Application Data

(60) Provisional application No. 61/583,760, filed on Jan. 6, 2012.

(51) Int. Cl.
   *G06G 7/48* (2006.01)
   *G06F 17/50* (2006.01)
   (Continued)

(52) U.S. Cl.
   CPC ............... *G06F 17/50* (2013.01); *G01V 1/30* (2013.01); *A61B 6/5217* (2013.01); *A61B 8/5223* (2013.01)

(58) Field of Classification Search
   CPC .. G06F 17/5009; G06F 2217/16; G06F 17/50; G01V 11/00; G01V 11/007; E21B 43/00
   (Continued)

(56) References Cited

U.S. PATENT DOCUMENTS

2007/0237419 A1* 10/2007 Shechtman et al. .......... 382/278
2012/0065888 A1* 3/2012 Wu et al. ........................ 702/8
2014/0056481 A1 2/2014 Zhdanov et al.

OTHER PUBLICATIONS

Stefano et al. "Multiple-domain, simultaneous joint inversion of geophysical data with application to subsalt imaging", Geophysics, vol. 76, Issue 3, May-Jun. 2011, p. R69-R80.*
(Continued)

*Primary Examiner* — Hugh M Jones
(74) *Attorney, Agent, or Firm* — Ray Quinney & Nebeker P.C.; Paul N. Taylor

(57) ABSTRACT

A method for the simultaneous imaging of different physical properties of an examined medium from the simultaneous joint inversion of multiple datasets of physical field measurements is described. The method introduces Gramian spaces of model parameters and/or their transforms, and Gramian constraints computed as the determinants of the corresponding Gram matrices of the model parameters and/or their transforms. Gramian constraints are introduced as additional regularization terms, and their minimization enforces the correlation between different model parameters and/or their transforms. The method does not require a priori knowledge about specific analytical or empirical or statistical correlations between the different model parameters and/or their attributes, nor does the method require a priori knowledge about specific geometric correlations between different model parameters and/or their attributes. The method is a generalized in that it can be applied to the simultaneous joint inversion of any number and combination of physical field measurements.

20 Claims, 10 Drawing Sheets

(51) Int. Cl.
  *G01V 1/30* (2006.01)
  *A61B 6/00* (2006.01)
  *A61B 8/08* (2006.01)
(58) Field of Classification Search
  USPC .................................................. 703/2, 6, 10
  See application file for complete search history.

(56) References Cited

OTHER PUBLICATIONS

U.S. Appl. No. 61/583,760, filed Jan. 6, 2012, Zhdanov.
U.S. Appl. No. 61/692,799, filed Aug. 24, 2012, Zhdanov et al.
U.S. Appl. No. 13/974,949, filed Jan. 5, 2012, Notice of Allowance.

* cited by examiner

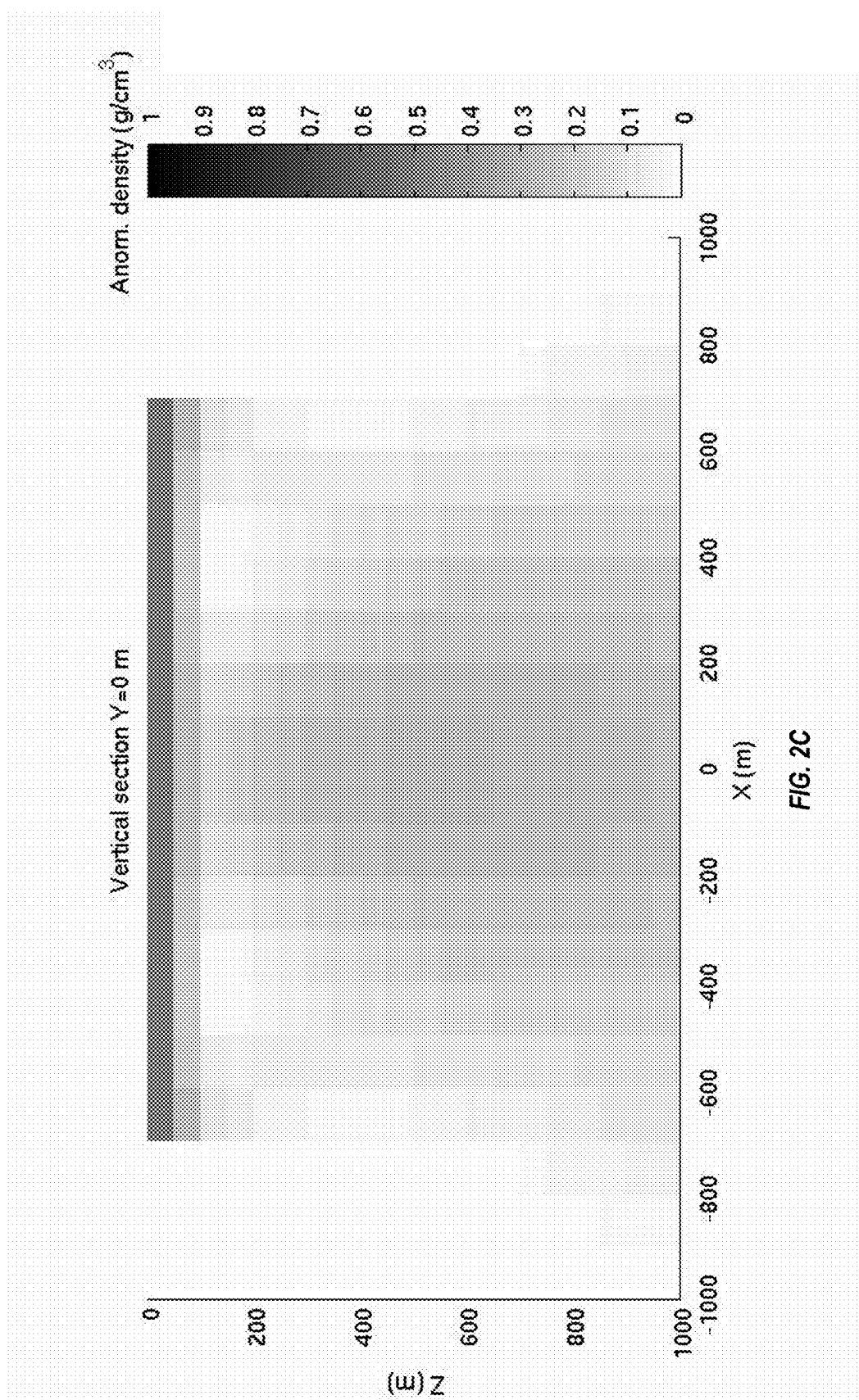

METHOD OF SIMULTANEOUS IMAGING OF DIFFERENT PHYSICAL PROPERTIES USING JOINT INVERSION OF MULTIPLE DATASETS

CROSS-REFERENCE TO RELATED APPLICATIONS

This application claims the benefit of and priority to U.S. Provisional Application No. 61/583,760, filed Jan. 6, 2012, which is incorporated herein by reference in its entirety.

This application hereby incorporates the following publications by reference in their entirety: Zhdanov, M. S., 2002, Geophysical inverse theory and regularization problems: Elsevier.

BACKGROUND OF THE INVENTION

1. The Field of the Invention

The present disclosure relates in general to the simultaneous imaging of different physical properties of an examined medium from the joint inversion of multiple datasets of physical field measurements, as occurs in geophysical exploration, nondestructive testing, and medical imaging.

2. The Related Technology

In resource exploration, it is uncommon for any single geophysical method to discriminate economic geology. Data from multiple geophysical surveys spanning gravity, magnetic, electromagnetic, and seismic methods are often interpreted to infer geology from models of different physical properties. In many cases, the various geophysical data are complimentary, making it natural to propose a formal mathematical framework for their joint inversion to a self-consistent, shared earth model.

Different approaches to the joint inversion of geophysical data have been discussed in the literature. The simplest case of joint inversion is where the physical properties of the earth model are identical between different geophysical methods, such as the joint inversion of a DC resistivity survey and a time-domain electromagnetic survey for a common conductivity model. In another case, joint inversion may infer theoretical, empirical or statistical correlations between different physical properties, such as statistical relations between the resistivity and seismic velocity to jointly invert electromagnetic and seismic data for a common rock physics model. In yet another case, the different physical properties are not correlated but nevertheless have similar structural constraints such as seismic and resistivity defining a hydrocarbon reservoir container, so joint inversion can be formulated as a minimization of the cross-gradients between different physical properties (Colombo et al., 2010, U.S. Pat. No. 7,805,250 B2).

Existing methods of joint inversion are inadequate for capturing geological complexity. For example, analytic, empirical or statistical correlations between different physical properties may exist for all or only part of the shared earth model, and their specific form may be unknown. As another example, structures that are present in the data of one geophysical method may not be present in the data of another geophysical method, such as a change in acoustic impedance and lack of a resistivity gradient across a change in lithological facies. As yet another example, there may exist any combination of analytic, empirical or statistical correlations with structural correlations between different model parameters and/or different attributes of the model parameters. There remains a requirement to develop a generalized method of joint inversion which would not require a priori knowledge about specific analytical or empirical or statistical relationships between the different model parameters and/or their attributes.

BRIEF SUMMARY

The embodiments disclosed herein are related to systems, methods, and computer readable medium for simultaneous imaging of different physical properties of an examined medium from the simultaneous joint inversion of multiple datasets of physical field/signal measurements. In the systems, methods, and computer readable medium at least one component of at least two physical fields and/or signals with at least two sensors of corresponding physical fields and/or signals, generated by natural or artificial (controlled) sources, placed at some proximity of the examined medium are measured. The observed data is recorded by a corresponding recording device. A Gramian space of model parameters and/or their transforms and/or their attributes, formed by integrable functions describing corresponding model parameters within a volume, V, of the examined medium with an inner product operation defined by a corresponding Gram matrix is constructed. A nonnegative Gramian functional equal to the determinant of the Gram matrix of at least two model parameters and/or their attributes is determined. Smoothing or focusing stabilizing functionals for producing smooth inverse images or images with sharp boundaries are determined. A parametric functional defined as a linear combination of misfit functionals for at least two datasets, smoothing or focusing stabilizing functional, and the Gramian functional is constructed. Multimodal model parameters, which correspond to the minimum of the parametric functional, are determined by solving a minimization problem for the parametric functional using linear and/or nonlinear optimization methods.

BRIEF DESCRIPTION OF THE DRAWINGS

FIGS. 2a-2d illustrates an example of a method of simultaneous imaging of the density and susceptibility parameters of the subsurface from the joint inversion of observed gravity and magnetic data.

DETAILED DESCRIPTION

Figure 1:
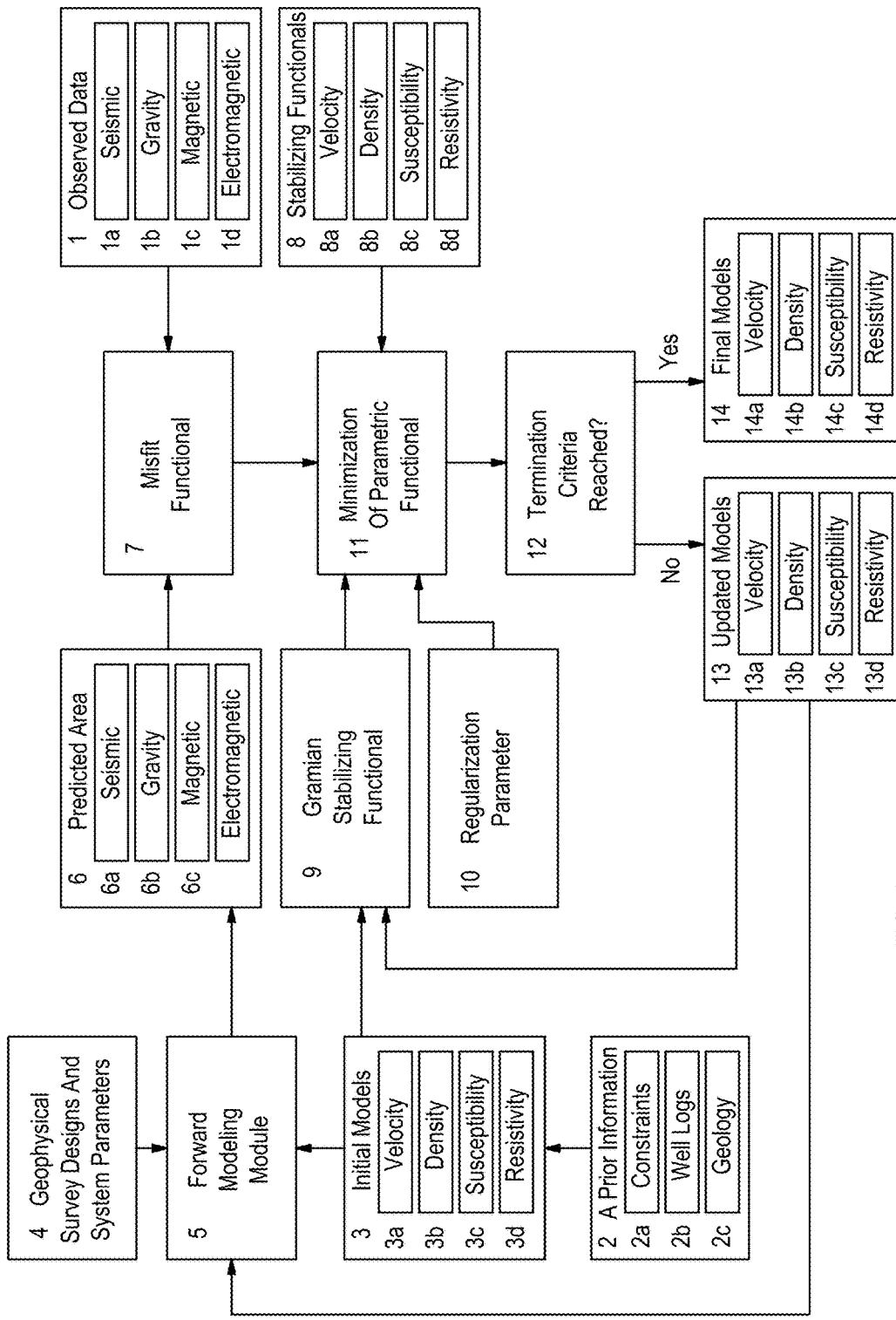
FIG. 1 illustrates an embodiment of the method of imaging of different physical properties of a target, where a data acquisition system with the sensors of the different physical fields and/or signals is located at some proximity of the examined medium.
Figure 2A:
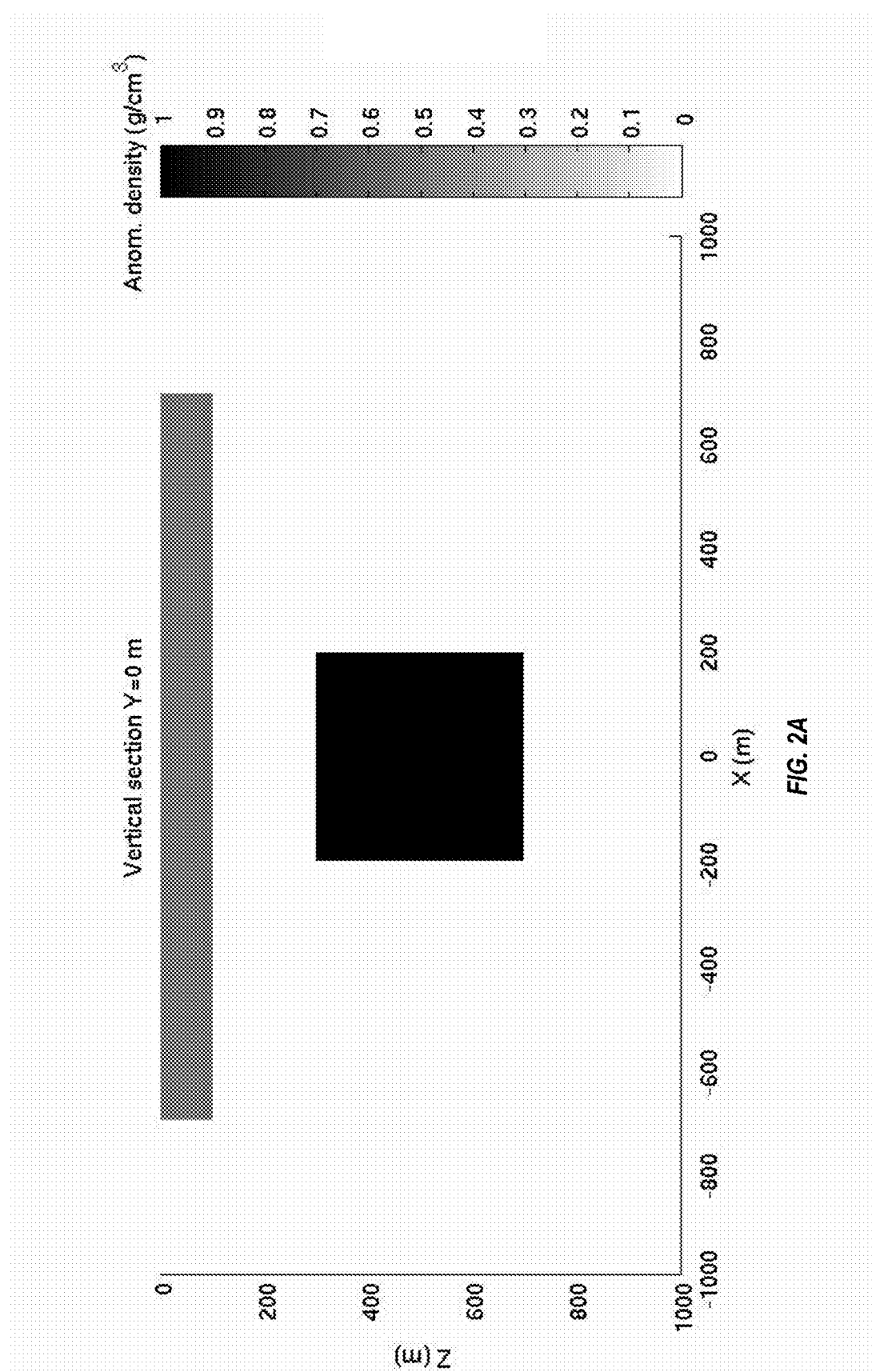
Figure 2B:
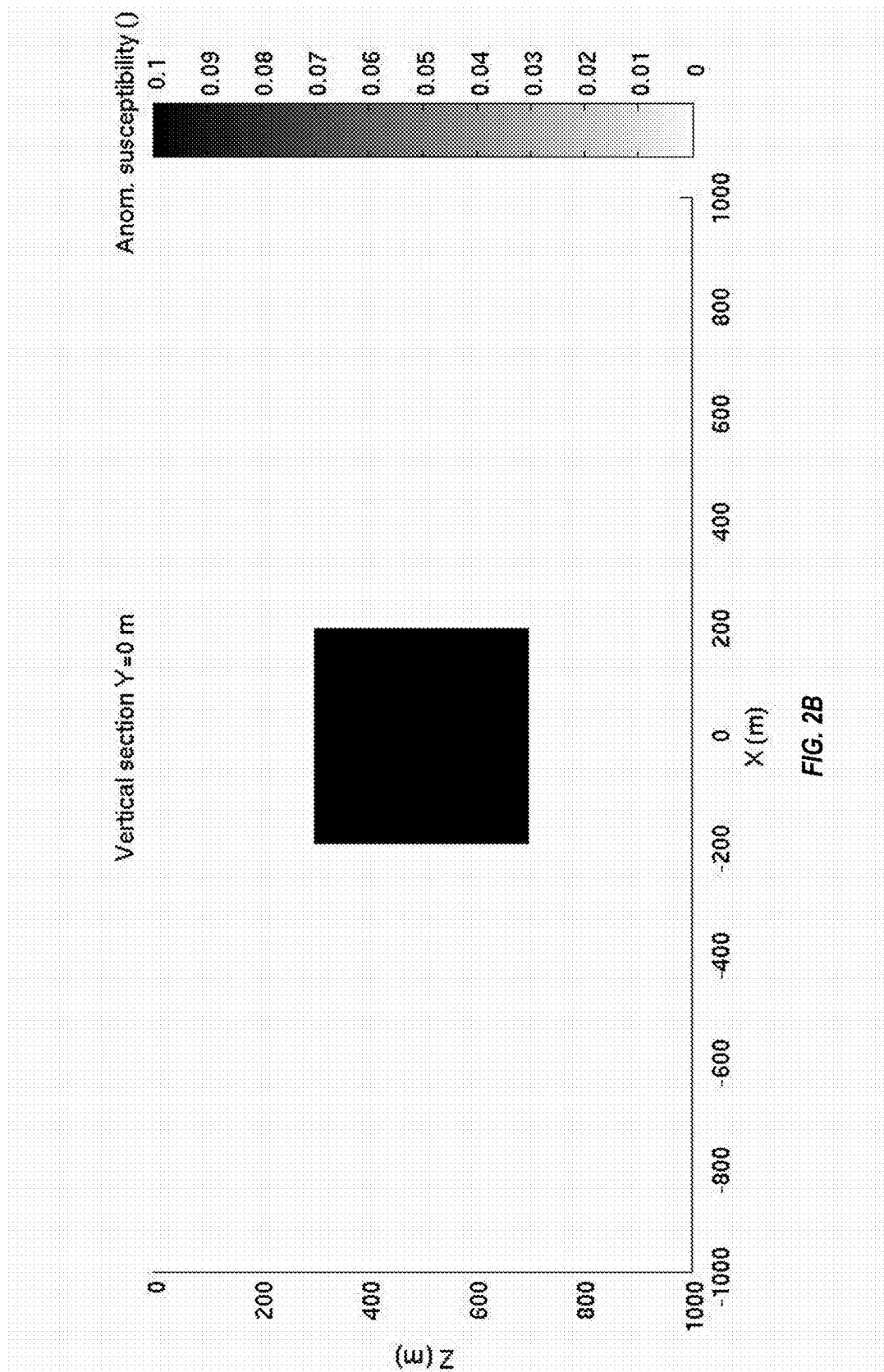
Figure 2D:
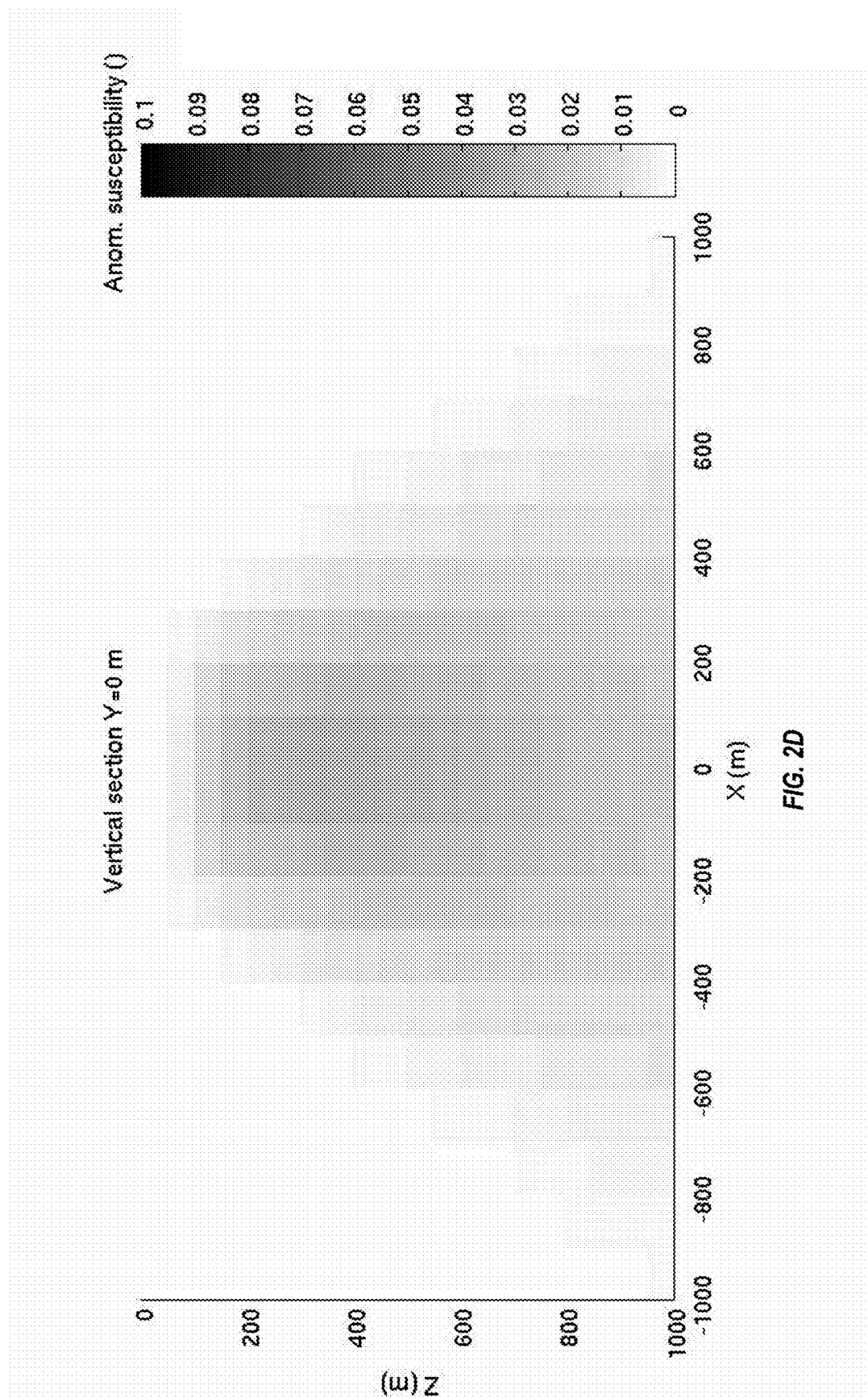
Figure 3A:
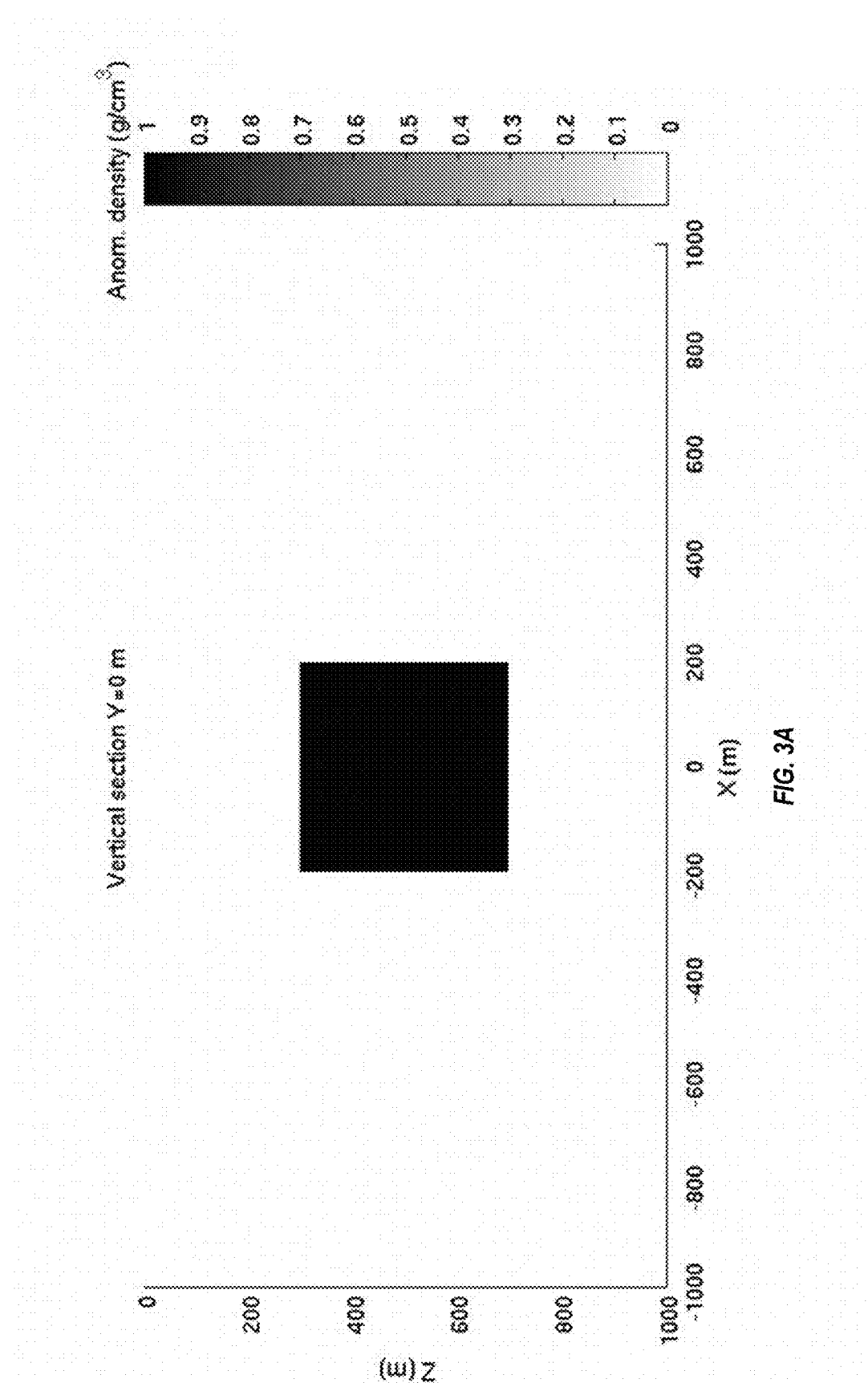
FIGS. 3a-3d illustrates another example of a method of simultaneous imaging of the density and susceptibility parameters of the subsurface from the joint inversion of observed gravity and magnetic data.
Figure 3B:
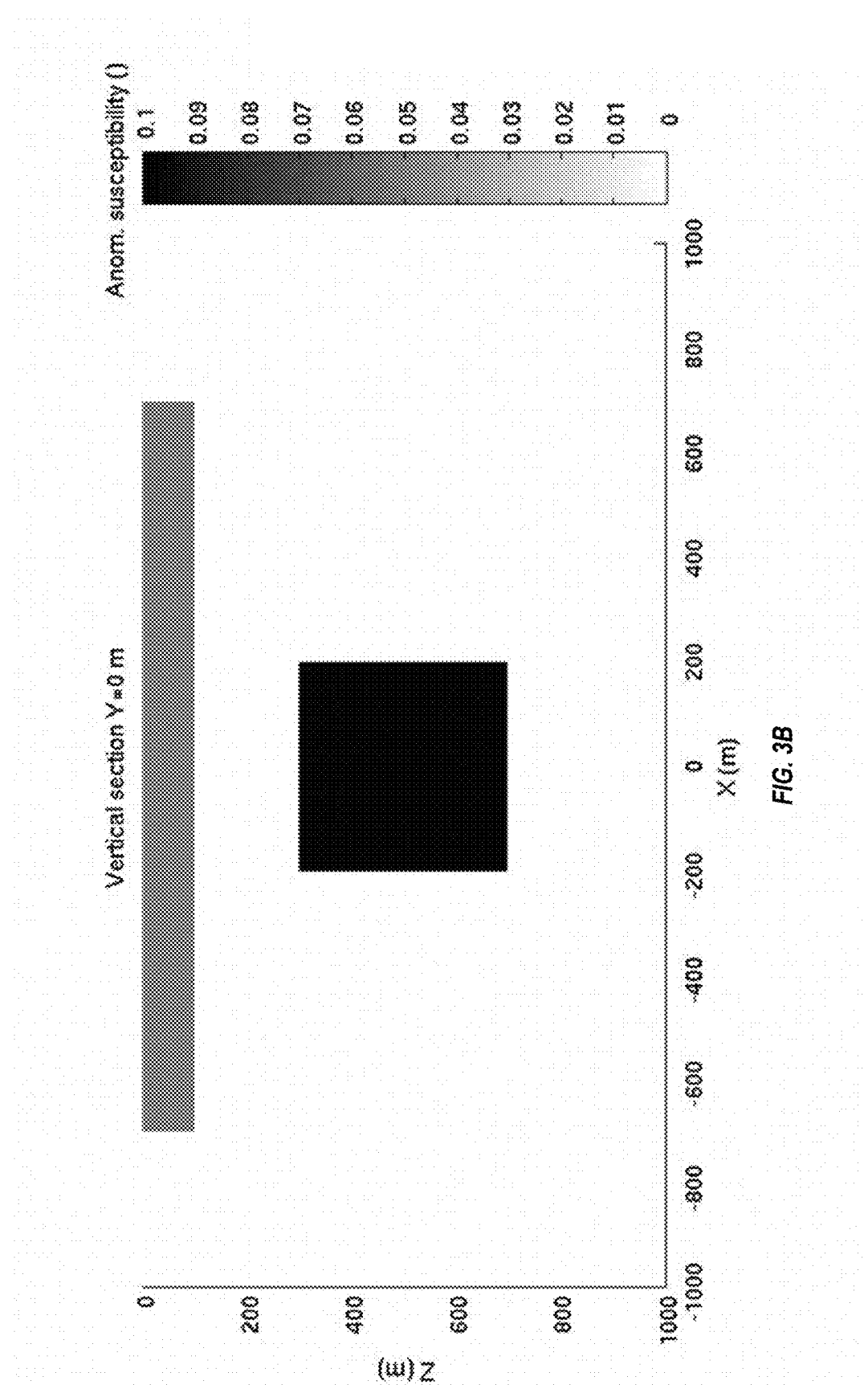
Figure 3C:
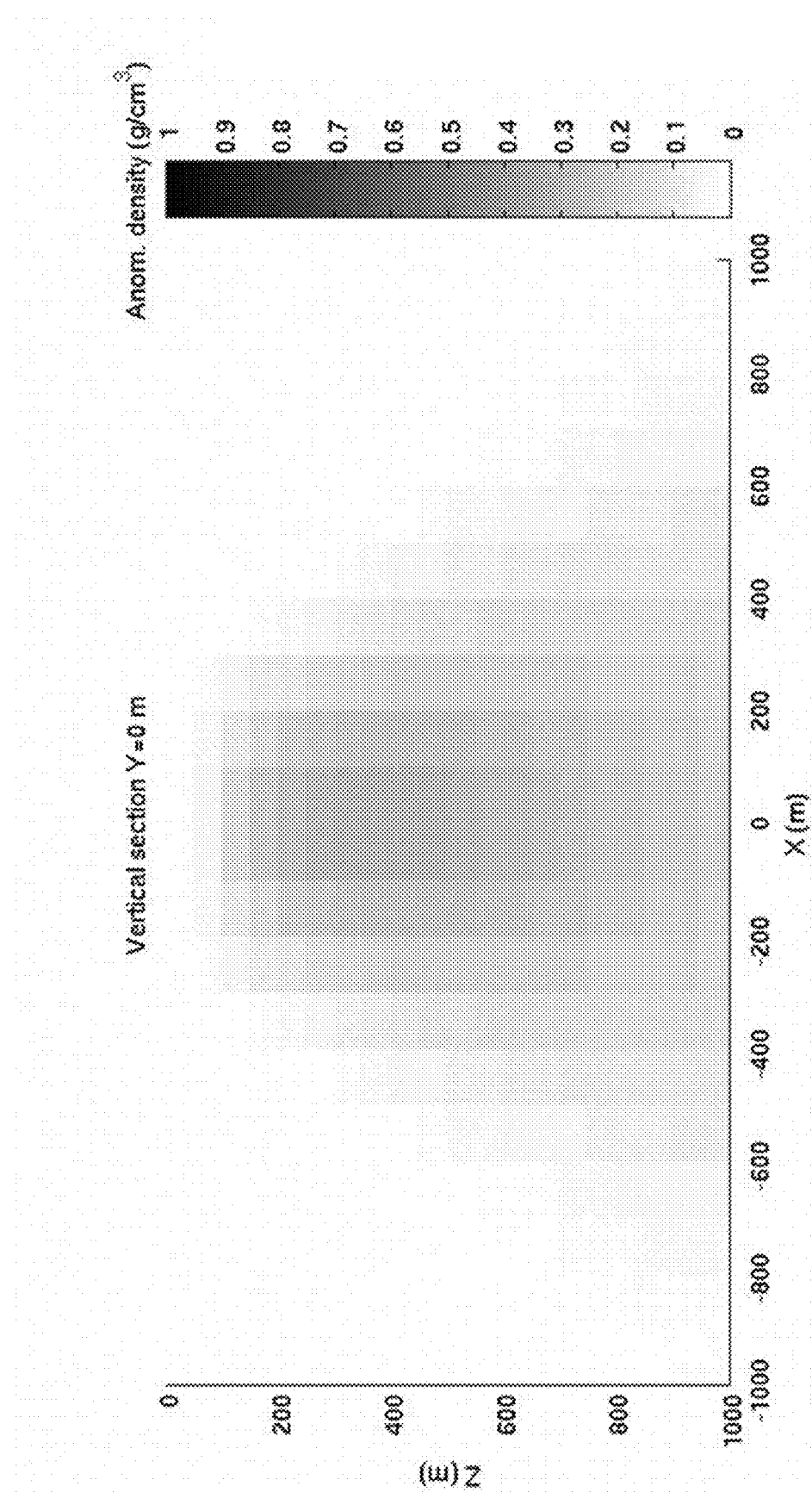
Figure 3D:
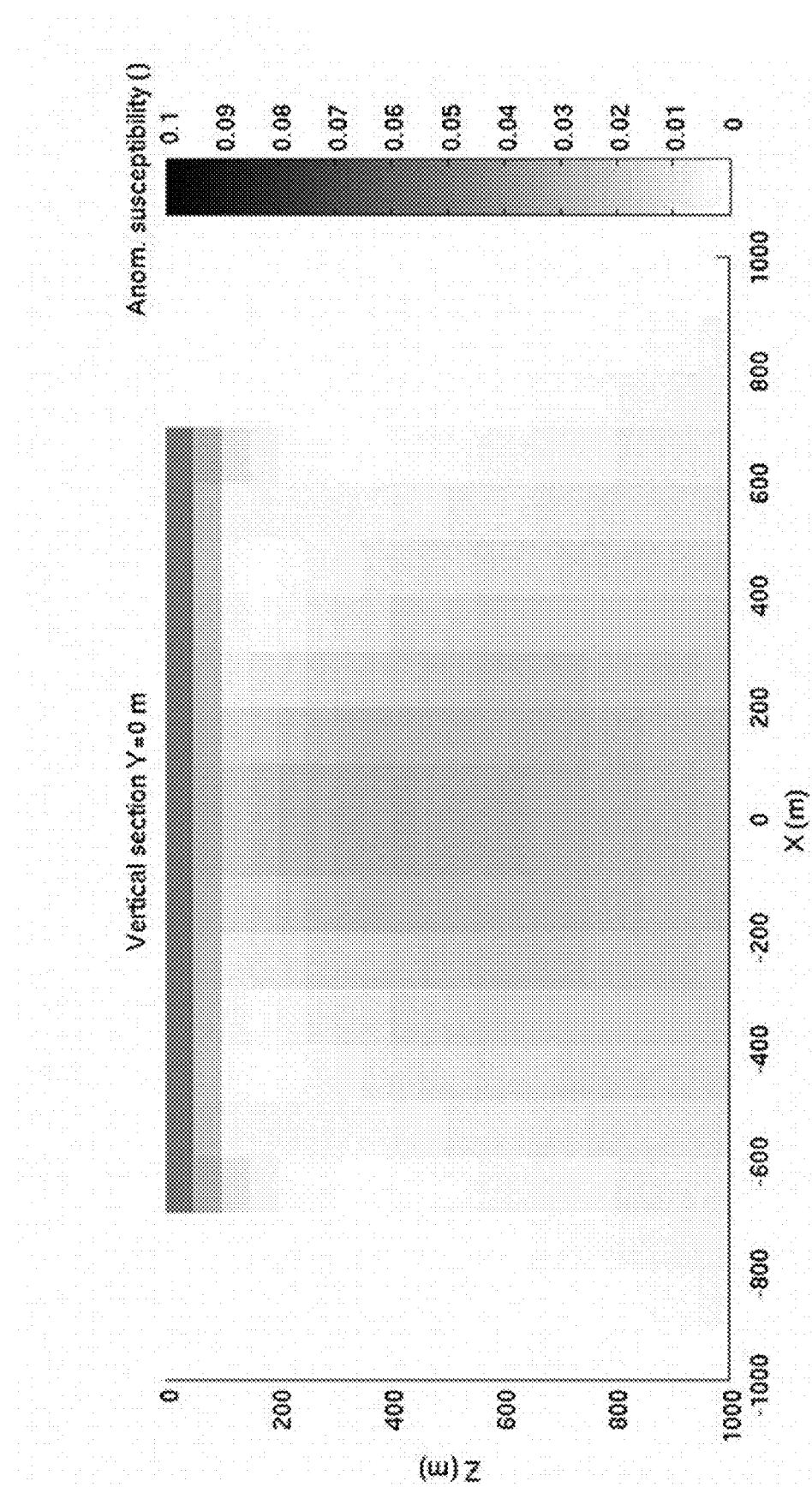

At least one embodiment of the method disclosed herein can be applied for the simultaneous imaging of different physical properties of the subsurface for mineral, hydrocarbons, geothermal and groundwater exploration, solid earth processes, unexploded ordinance detection, underground structures and tunnel detection, anti-submarine warfare, and environmental monitoring, from the joint inversion of multiple datasets, such as thermal, gravity, magnetic, electrical, electromagnetic, and seismic data.

Another embodiment of the method disclosed herein can be applied for the simultaneous imaging of different physical properties of a body for medical imaging, from the joint inversion of multiple datasets, such as x-ray, magnetic resonance, ultrasound, electrical, and radionuclide data.

At least one embodiment of the method disclosed herein is based on calculating a nonnegative Gramian functional equal to the determinant of the Gram matrix of the model parameters and/or different functions of the model parameters. Note that, the determinant of the Gram matrix characterizes the degree of the linear dependency between the different model parameters, $m^{(1)}, m^{(2)}, \ldots,$ and $m^{(n)}$. Thus, minimization of this function results in enforcing of the correlation between the different model parameters.

Another embodiment of the method disclosed herein is based on calculating a nonnegative Gramian functional equal to the determinant of the Gram matrix of the transformed model parameters and/or different functions of the transformed model parameters. In this case, the determinant of the Gram matrix characterizes the degree of the linear dependency between the different transformed model parameters, $Tm^{(1)}, Tm^{(2)}, \ldots,$ and $Tm^{(n)}$, where T is the transform operator and may be chosen as a model weighting operator, a differential operator (e.g., gradient or Laplacian), an absolute value of the model parameters or their differential operators, a Fourier transform, a logarithm, an exponential, or any other transform which emphasize specific properties (attributes) of the model parameters. Thus, minimization of the Gramian functional results in enforcing of the correlation between the different transformed model parameters and/or their attributes.

An important characteristic of the method disclosed herein is that it does not require any knowledge about any specific analytical, empirical or statistical relationships between the different model parameters and/or their attributes, but relies instead on general evaluation of the degree of existence of these relationships.

In yet another embodiment of the present invention, the structural similarity between different model parameters is based on calculating a nonnegative Gramian functional equal to the determinant of the Gram matrix of the model parameters and/or different functions of the spatial gradients of the model parameters. In this case, the determinant of the Gram matrix characterizes the degree of correlation between the spatial gradients of the different model parameters, $\nabla m^{(1)}, \nabla m^{(2)}, \ldots,$ and $\nabla m^{(n)}$. Thus, minimization of this function results in enforcing of the structural (geometric) similarity between the different images.

More specifically, a method of the present disclosure is based on measuring at least two datasets representing different model parameters of the examined medium; introducing the Gramian space of the model parameters and/or their transforms and/or their attributes, formed by the integrable functions describing the corresponding model parameters within a volume, V, of the examined medium with the inner product operation defined by the corresponding Gram matrix; determining a nonnegative Gramian functional equal to the determinant of the Gram matrix of at least two model parameters and/or their attributes; determining another nonnegative Gramian functional equal to the determinant of the Gram matrix of at least two transformed model parameters and/or their attributes; determining another Gramian functional equal to the determinant of the Gram matrix of the spatial gradients of the model parameters and/or their attributes; determining smoothing or focusing stabilizing functionals for producing smooth inverse images or the images with sharp boundaries as described in Zhdanov [2002]; as described constructing a parametric functional defined as a linear combination of the misfit functionals for at least two datasets, smoothing or focusing stabilizing functional, and at least one of the Gram functionals introduced above; determining the model parameters, which correspond to the minimum of the parametric functional, by solving a minimization problem for the parametric functional using linear and/or nonlinear optimization methods.

In a method of the present disclosure, external constraints on the model parameters, including but not limited to a priori models and/or upper and/or lower bounds, can be applied to the joint inversion and may consist of a priori knowledge of the model parameters and/or their attributes (e.g., from well logs or laboratory analysis of rock samples), and the interpretative knowledge about model parameters and/or their attributes (e.g., from geological interpretation).

In methods of the present disclosure, the dimensionality of the model parameters and/or their attributes may be one-dimensional, two-dimensional, three-dimensional, or four-dimensional.

In at least one embodiment of a method disclosed herein, the geophysical data are inclusive of any combination of thermal and/or gravity and/or magnetic and/or electrical and/or electromagnetic and/or seismic and/or nuclear data.

At least one embodiment of a method disclosed herein can be applied for the imaging of geological formations and/or man-made objects for mineral, hydrocarbon, geothermal and groundwater exploration, in-situ mining, hydrocarbon, geothermal and groundwater resource monitoring, unexploded ordinance (UXO), improvised explosive device (IED), tunnel, and underground facility (UGF) detection, anti-submarine warfare, geosteering, bathymetry mapping, ice thickness mapping, and environmental monitoring.

At least one embodiment of this method can be used in geophysical exploration for mineral, hydrocarbon, geothermal, and groundwater resources, and solid earth processes.

At least one embodiment of this method can be used in geophysical monitoring for in-situ mining, hydrocarbon, geothermal, and groundwater resources, and solid earth processes.

At least one embodiment of this method can be used for detecting UXO, IEDs, tunnels, and UGFs.

At least one embodiment of this method can be used for geosteering.

At least one embodiment of this method can be used for formation evaluation and/or logging-while-drilling (LWD) and/or measurement-while-drilling (MWD) and/or imaging-while-drilling (IWD).

At least one embodiment of this method can be used for mapping bathymetry in shallow and/or temporal and/or turbid water.

At least one embodiment of this method can be used for mapping ice thickness.

At least one embodiment of this method can be used for environmental monitoring, such as salinity, acid mine drainage, and pollution plumes.

At least one embodiment of this method can be used for anti-submarine warfare.

In at least one embodiment of a method disclosed herein, the medical data are inclusive of any combination of x-ray and/or magnetic resonance and/or ultrasound and/or electrical and/or radionuclide data.

At least one embodiment of a method disclosed herein, can be applied to the imaging of bodies.

Figure 4:
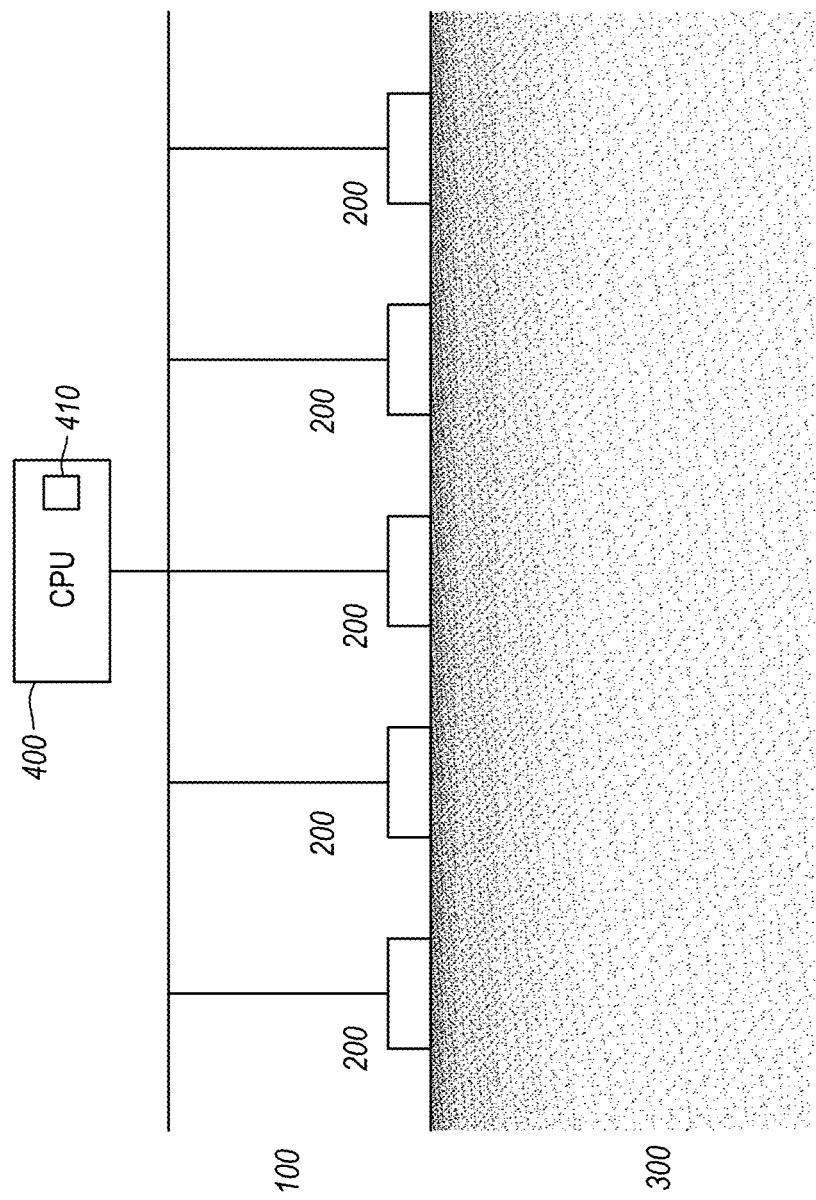
FIG. 4 illustrates a data acquisition system according to the embodiments disclosed herein.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein reference numerals designate corresponding parts in the various figures. It is to be expressly understood, however, that the drawings are for the purpose of illustration and description only, and are not intended as a definition of the limits of the invention. As used in the specification and in the claims, the singular form of "a", "an" and "the" include plural referents unless the context clearly dictates otherwise. Attention is first given to FIG. 4, which illustrates an embodiment of a data acquisition system 100 that may be used to practice the embodiments disclosed herein. The data acquisition system 100 may include one or more sensors of different physical fields and/or signals 200 that are located at some proximity of an examined medium 300. In one embodiment, the sensors 200 may be arranged as an array on the surface or within the examined medium 300. It will be appreciated that the sensors 200 may be arranged in any reasonable manner. In some embodiments, the sensors 200 may be seismic, electric, magnetic, gravity, acoustic, and/or temperature field sensors or any combination thereof. In other embodiments, the sensor 200 may be optical, electromagnetic, elastic, and/or radio wave signal sensors or any combination thereof. In still other embodiments, the sensor 200 may be x-ray, magnetic resonance, ultrasound, electrical and/or radionuclide sensors. It will be appreciated that the sensors 200 may be any reasonable type of sensor or combination of sensors as circumstances warrant.

In one embodiment, the sensors 200 may record at least one component of corresponding physical fields and/or signals, generated as a response from the examined medium 300 to the natural or artificial (controlled) sources. In some embodiments a processor 400, which may include, for example, a central processing unit, may operate the data acquisition system. The processor 400 may include a recording device 410 for recording the data measured or obtained by the sensor One embodiment of a method of simultaneous imaging different physical properties of an examined medium from the joint inversion of observed data from multiple geophysical field measurements is shown in FIG. 1. Observed geophysical data 1 may include but not be limited to seismic 1a, gravity 1b, magnetic 1c, and electromagnetic 1d data, and may be measured above and/or on the surface of and/or within the subsurface. A priori information about the subsurface 2 may include constraints on the physical properties 2a, well logs 2b, and interpreted geology 2c. A priori information about the subsurface 2 may be used to construct initial models 3 for each of the different physical properties, such as seismic compressional and/or shear velocity 3a, density 3b, magnetic susceptibility and/or magnetization 3c, and resistivity and/or conductivity 3d. Emulating the geophysical survey design and system parameters 4, a forward modeling module 5 can be used to calculate the predicted geophysical data 6 including but not limited to seismic 6a, gravity 6b, magnetic 6c, and electromagnetic 6d data.

A misfit functional 7 calculates the misfit and residual vector between at least two observed geophysical data 1 and predicted geophysical data 6. Stabilizing functionals 8 are calculated for at least two model parameters and/or their attributes, and may include any smooth or focusing stabilizing functions such as Laplacian, minimum gradient, minimum norm, minimum support, minimum gradient support, or minimum gradient support.

A Gramian stabilizing functional 9 is calculated as the nonnegative Gramian functional equal to the determinant of the Gram matrix of at least two model parameters and/or their attributes, or as the nonnegative Gram functional equal to the determinant of the Gram matrix of at least two transformed model parameters and/or their attributes, or as a Gramian functional equal to the determinant of the Gram matrix of the spatial gradients of the model parameters and/or their attributes. A regularization parameter 10 is predetermined or calculated using standard principles of regularization theory.

A parametric functional is constructed as the linear combination of the misfit functional, at least one stabilizing functional introduced above, and at least one Gramian stabilizing functional introduced above. The parametric functional is minimized using a linear or nonlinear optimization method 11, such as a regularized conjugate gradient method. The termination criteria of the joint inversion 12 is evaluated, such as a predetermined misfit being achieved. If the termination criteria are not satisfied, the model parameters are updated as updated model parameters 13, and the aforementioned joint inversion process is reiterated. If the termination criteria are satisfied, the model parameters are updated as final model parameters 14, and the joint inversion process is terminated.

In some embodiments, the simultaneous imaging of different physical properties of an examined medium from the joint inversion of observed data from multiple geophysical field measurements may be achieved using the processor 400, which may include, for example, a central processing unit, a storage system, and a communications system. The processor 400 may be distributed across one or more processors.

EXAMPLE 1

The following is an example of at least some of the principles of the method of simultaneous imaging of different physical properties of an examined medium from the joint inversion of multiple datasets of physical field measurements. It is not intended thereby to limit the scope of the disclosure to any particular theory of operation or to any field of application.

In general, we can consider the modeling of multiple physical fields as the operator relationships:

$$A^{(i)}(m^{(i)})=d^{(i)}, i=1, 2, \ldots, n, \qquad (1)$$

where, in a general case, $A^{(i)}$ is a nonlinear operator, $m^{(i)}$ are the unknown model parameters which form a complex Hilbert space of model parameters, M, with an $L_2$ norm defined by the corresponding inner product:

$$(m^{(i)}, m^{(j)})_M = \int_V m^{(i)}(r) m^{(j)*}(r) dv, \|m^{(i)}\|_M^2 = (m^{(i)}, m^{(i)})_M, \qquad (2)$$

In equation (2), r is a radius vector defined within a volume, V; the asterisk * denotes the complex conjugate; and $d^{(i)}$ are different observed data that belong to a complex Hilbert space of data, D, with an $L_2$ norm defined by the corresponding inner product:

$$(d^{(i)}, d^{(j)})_D = \int_S d^{(i)}(r) d^{(j)*}(r) dv, \|d^{(i)}\|_D^2 = (d^{(i)}, d^{(i)})_D, \qquad (3)$$

where S is an observation surface.

Let us consider two arbitrary functions from the model space, $p(r), q(r) \in M$. We introduce a new inner product operation, $(p, q)_{G^{(n)}}$, between the two functions as the matrix determinant:

$$(p, q)_{G^{(n)}} = \begin{vmatrix} (m^{(1)}, m^{(1)})_M & (m^{(1)}, m^{(2)})_M & \cdots & (m^{(1)}, m^{(n-1)})_M & (m^{(1)}, q)_M \\ (m^{(2)}, m^{(1)})_M & (m^{(2)}, m^{(2)})_M & \cdots & (m^{(2)}, m^{(n-1)})_M & (m^{(2)}, q)_M \\ \vdots & \vdots & \ddots & \vdots & \vdots \\ (m^{(n-1)}, m^{(1)})_M & (m^{(n-1)}, m^{(2)})_M & \cdots & (m^{(n-1)}, m^{(n-1)})_M & (m^{(n-1)}, q)_M \\ (p, m^{(1)})_M & (p, m^{(2)})_M & \cdots & (p, m^{(n-1)})_M & (p, q)_M \end{vmatrix}, \quad (4)$$

where all properties of the inner product hold:

$$(p, q)_{G^{(n)}} = (q, p)^*_{G^{(n)}}, \quad (5)$$

$$(\alpha_1 p^{(1)} + \alpha_2 p^{(2)}, q)_{G^{(n)}} = \alpha_1 (p^{(1)}, q)_{G^{(n)}} + \alpha_2 (p^{(2)}, q)_{G^{(n)}}, \quad (6)$$

$$(p, p)_{G^{(n)}} \geq 0. \quad (7)$$

The last property (7) follows from the fact that the norm square of a function, $\|p\|_{G^{(n)}}^2$, is equal to the determinant, $G(m^{(1)}, m^{(2)}, \ldots, m^{(n-1)}, p)$, of the Gram matrix of a system of functions, $(m^{(1)}, m^{(2)}, \ldots, m^{(n-1)}, p)$, which is called a Gramian:

$$\|p\|_{G^{(n)}}^2 = (p, p)_{G^{(n)}} \quad (8)$$
$$= G(m^{(1)}, m^{(2)}, \ldots m^{(n-1)}, p)$$
$$= \begin{vmatrix} (m^{(1)}, m^{(1)})_M & (m^{(1)}, m^{(2)})_M & \cdots & (m^{(1)}, m^{(n-1)})_M & (m^{(1)}, p)_M \\ (m^{(2)}, m^{(1)})_M & (m^{(2)}, m^{(2)})_M & \cdots & (m^{(2)}, m^{(n-1)})_M & (m^{(2)}, p)_M \\ \vdots & \vdots & \ddots & \vdots & \vdots \\ (m^{(n-1)}, m^{(1)})_M & (m^{(n-1)}, m^{(2)})_M & \cdots & (m^{(n-1)}, m^{(n-1)})_M & (m^{(n-1)}, p)_M \\ (p, m^{(1)})_M & (p, m^{(2)})_M & \cdots & (p, m^{(n-1)})_M & (p, p)_M \end{vmatrix}.$$

The Gramian satisfies Gram's inequality:

$$G(m^{(1)}, m^{(2)}, \ldots, m^{(n-1)}, p) \geq 0. \quad (9)$$

which holds even if the system of functions $(m^{(1)}, m^{(2)}, \ldots, m^{(n-1)}, p)$ is linearly dependent.

A Gramian space of the model parameters, $G^{(n)}$, is the Hilbert space formed by the integrable functions, defined within a volume, V, with the inner product operation defined by equation (4). The main property of the Gramian space is that the norm of a function, p, in the Gramian space provides a measure of correlation between the function and the model parameters, $m^{(1)}, m^{(2)}, \ldots m^{(n-1)}$.

Similarly, one can introduce a Gramian space $G^{(j)}$, where the inner product is defined in a similar manner to equation (8), with the only difference that the functions p and q are located within the row and column j, respectively:

$$(p, q)_{G^{(j)}} = \quad (10)$$

$$\begin{vmatrix} (m^{(1)}, m^{(1)})_M & (m^{(1)}, m^{(2)})_M & \cdots & (m^{(1)}, q)_M & (m^{(1)}, m^{(n)})_M \\ \vdots & \vdots & \cdots & \vdots & \vdots \\ (p, m^{(1)})_M & (p, m^{(2)})_M & \ddots & (p, q)_M & (p, m^{(n)})_M \\ \vdots & \vdots & \cdots & \vdots & \vdots \\ (m^{(n)}, m^{(1)})_M & (m^{(n)}, m^{(2)})_M & \cdots & (m^{(n)}, q)_M & (m^{(n)}, m^{(n)})_M \end{vmatrix}.$$

In the Gramian space, $G^{(j)}$, the norm square of a function $\|p\|_{G^{(j)}}^2$, is equal to the Gramian of a system of functions $(m^{(1)}, m^{(2)}, \ldots, m^{(j-1)}, p, m^{(j+1)}, \ldots m^{(n)})$:

$$\|p\|_{G^{(j)}}^2 = (p, p)_{G^{(j)}} = G(m^{(1)}, m^{(2)}, \ldots, m^{(j-1)}, p, m^{(j+1)}, \ldots m^{(n)}). \quad (11)$$

The norm of the function in the Gramian space, $G^{(j)}$, provides a measure of the correlation between this function and all other model parameters, with the exception of parameter $\tilde{m}^{(j)}$. This Gramian norm has the following property:

$$\|m^{(i)}\|_{G^{(j)}}^2 = \|m^{(j)}\|_{G^{(i)}}^2, \quad (12)$$

for $i=1, 2, \ldots, n$, and $j=1, 2, \ldots, n$. Equation (12) demonstrates that all functions have the same norm in the corresponding Gramian spaces, $G^{(j)}$, $j=1, 2, \ldots, n$.

The use of Gramian constraints can be generalized to make it possible to introduce any function of the model parameters. We do this by introducing a transform operator, T, of the model parameters from model space, M, to the transformed model space, $M_T$:

$$f = Tp, \quad (13)$$

$$g = Tq, \quad (14)$$

where $p, q \in M$, $f, g \in M_T$. The transform operator, T, can be chosen as a differential operator (e.g., gradient or Laplacian), an absolute value of the model parameters or their derivatives, a Fourier transform, a logarithm, an exponential, or any other transform which emphasizes specific properties of the models. We consider all transformations as attributes of the model parameters.

Consider two arbitrary functions from the transformed model space with a given inner product operation:

$$(f, g)_{M_T} = \int_V f(r) g^*(r) dv. \quad (15)$$

One can introduce an inner product operation, $$(f, g)_{G_T^{(n)}},$$

between the two functions as the matrix determinant:

$$(f, g)_{G_T^{(n)}} = \begin{vmatrix} (Tm^{(1)}, Tm^{(1)})_{M_T} & (Tm^{(1)}, Tm^{(2)})_{M_T} & \ldots & (Tm^{(1)}, Tm^{(n-1)})_{M_T} & (Tm^{(1)}, g)_{M_T} \\ (Tm^{(2)}, Tm^{(1)})_{M_T} & (Tm^{(2)}, Tm^{(2)})_{M_T} & \ldots & (Tm^{(2)}, Tm^{(n-1)})_{M_T} & (Tm^{(2)}, g)_{M_T} \\ \vdots & \vdots & \ddots & \vdots & \vdots \\ (Tm^{(n-1)}, Tm^{(1)})_{M_T} & (Tm^{(n-1)}, Tm^{(2)})_{M_T} & \ldots & (Tm^{(n-1)}, Tm^{(n-1)})_{M_T} & (Tm^{(n-1)}, g)_{M_T} \\ (f, Tm^{(1)})_{M_T} & (f, Tm^{(2)})_{M_T} & \ldots & (f, Tm^{(n-1)})_{M_T} & (f, g)_{M_T} \end{vmatrix}. \quad (16)$$

The norm square of a transformed function, $$\|Tp\|_{G_T^{(n)}}^2,$$

is equal to the Gramian of a system of transforms, $Tm^{(1)}$, $Tm^{(2)}$, ..., $Tm^{(n-1)}$, $Tp$:

$$\|Tp\|_{G_T^{(n)}}^2 = G(Tm^{(1)}, Tm^{(2)}, \ldots, Tm^{(n-1)}, Tp). \quad (17)$$

The norm of the transformed function p in the Gramian space provides a measure of the correlation between the transform of the function and similar transforms of the model parameters, $T\tilde{m}^{(1)}, T\tilde{m}^{(2)}, \ldots T\tilde{m}^{(n-1)}$. Minimization of the norm $$\|Tp\|_{G_T^{(n)}}^2$$

will result in multi-attributed models with correlated transforms of the model parameters.

As an example of one class of model parameter transforms, one can consider the gradients of the model parameters. While there may not be any correlations between different model parameters, there may be structural correlations of their distributions, which can be related in a Gramian space of model parameter gradients.

One can select the operator, T, as the gradient operator, $\nabla$. One can determine the inner product of two arbitrary gradient functions from the model space of gradients, $\nabla p(r)$, $\nabla q(r) \in M_\nabla$, as:

$$(\nabla p, \nabla q)_{M_\nabla} = \int_V \nabla p(r) \cdot \nabla q^*(r) dv, \quad (18)$$

According to equations (16) and (17), the norm square, $$\|\nabla p\|_{G_\nabla^{(n)}}^2,$$

of a gradient of a function in the corresponding Gramian space, $G_\nabla^{(n)}$, is equal to the Gramian of the system of gradients, $\nabla m^{(1)}, \nabla m^{(2)}, \ldots \nabla m^{(n-1)}, \nabla p$:

$$\|\nabla p\|_{G_\nabla^{(n)}}^2 = G(\nabla m^{(1)}, \nabla m^{(2)}, \ldots, \nabla m^{(n-1)}, \nabla p). \quad (17)$$

The norm of the gradient of a function, p, in the Gramian space provides a measure of correlation between the gradient of this function and the gradients of the model parameters, $\nabla m^{(1)}, \nabla m^{(2)}, \ldots, \nabla m^{(n-1)}$. Minimization of this norm, $$\|\nabla p\|_{G_T^{(n)}}^2,$$

will result in multi-attributed models with correlated gradients.

For regularized joint inversion with Gramian constraints, one needs to minimize a parametric functional with the Gramian stabilizers:

$$P^\alpha(m^{(1)}, m^{(2)}, \ldots, m^{(n)}) = \Sigma_{i=1}^n \|A^{(i)}(m^{(i)}) - d^{(i)}\|_D^2 + \alpha c_1 \Sigma_{i=1}^n S^{(i)} + \alpha c_2 S_G \to \min, \quad (20)$$

where $A^{(i)}(m^{(i)})$ are the predicted data, $\alpha$ is the regularization parameter, $S^{(i)}$ are smoothing or focusing stabilizing functionals, $S_G$ is the Gramian stabilizing functional for transformed model parameters:

$$S_G = \|Tm^{(n)}\|_{G_T^{(n)}}^2 = G(Tm^{(1)}, Gm^{(2)}, \ldots, Gm^{(n)}). \quad (21)$$

It is implied that the transform operator, T, may be the identity operator, and $c_1$ and $c_2$ are the weighting coefficients determining the weights of the different stabilizers in the parametric functional. Note that, according to the properties of the norm, $$\| \ldots \|_{G_T^{(n)}}^2,$$

in the Gramian space, $G_T^{(n)}$, minimization of this norm results in enforcing the correlation between different transforms (attributes) of the model parameters.

To minimize parametric functional (20), one can construct a regularized conjugate gradient (RCG) method, which for the $k^{th}$ iteration can be summarized as:

$$r_k = A(m_k) - d, \quad (22a)$$

$$l_k^\alpha = l^\alpha(m_k), \quad (22b)$$

$$\beta_k^\alpha = \|l_k^\alpha\|^2 / \|l_{k-1}^\alpha\|^2, \quad (22c)$$

$$\tilde{l}_k^\alpha = l_k^\alpha + \beta_k^\alpha \tilde{l}_{k-1}^\alpha, \quad (22d)$$

$$\tilde{s}_k^\alpha = (\tilde{l}_k^\alpha, l_k^\alpha) / \{\|\tilde{F}_{m_k} \tilde{l}_k^\alpha\|^2 + \alpha \|W \tilde{l}_k^\alpha\|^2\}, \quad (22e)$$

$$m_{k+1} = m_k - \tilde{s}_k^\alpha \tilde{l}_k^\alpha, \quad (22f)$$

where $d = (d^{(1)}, d^{(2)}, \ldots, d^{(n)})$ is the vector of observed data, $m_k = (m_k^{(1)}, m_k^{(2)}, \ldots, m_k^{(n)})$ the vector of model parameters, $A(m_k)$ is the vector of predicted data, and $l_k^\alpha$ is the vector of the direction of steepest ascent.

Expressions for the direction of steepest ascent, $l^{\alpha(i)}$, can be found from the first variation of the parametric functional (20):

$$\delta P^\alpha = 2\Sigma_{i=1}^n (F_m^{(i)} \delta m^{(i)}, A^{(i)} m^{(i)} - d^{(i)})_D + 2\alpha$$
$$(c_1 \Sigma_{i=1}^n \delta S^{(i)} + c_2 \delta S_{G_T}^{(i)}) = 2\Sigma_{i=1}^n (\delta m^{(i)}, l^{\alpha(i)}), \quad (23)$$

where $F_m^{(i)}$ is the linear operator of the Fréchet derivative of $A^{(i)}$.

One now finds the first variation of the Gramian stabilizing functional:

$$\delta S_{G_T}^{(i)} = \sum_{i=1}^n \delta_{m^{(i)}} \|Tm^{(n)}\|_{G_T^{(n)}}^2 \quad (24)$$
$$= \sum_{i=1}^n \delta_{m^{(i)}} \|Tm^{(i)}\|_{G_T^{(i)}}^2$$
$$= 2\sum_{i=1}^n (\delta m^{(i)}, l_{G_T}^{(i)}),$$

where property (12) of the Gramian norm is taken into account, and the first variation of the norm, $$\|Tm^{(i)}\|_{G_T^{(i)}}^2,$$

is calculated as:

$$\delta_{m^{(i)}} \|Tm^{(i)}\|_{G_T^{(i)}}^2 = 2\left(\delta m^{(i)}, \sum_{j=1}^n (-1)^{i+j} G_{ij}^{Tm} F_T^* Tm^{(j)}\right) \quad (25)$$
$$= 2(\delta m^{(i)}, l_{G_T}^{(i)}).$$

In equation (25), $G_{ij}^{Tm}$ is the corresponding minor of the Gram matrix G ($Tm^{(1)}, Tm^{(2)}, Tm^{(n)}$) formed by eliminating column i and row j, $F_T^*$ is the adjoint derivative of the transform operator, T, and vectors $l_{G_T}^{(i)}$ are the directions of steepest ascent for the Gramian stabilizing functionals, formed by the Gramian of the transformed model parameter:

$$l_{G_T}^{(i)} = \Sigma_{j=1}^n (-1)^{i+j} G_{ij}^{Tm} F_T^* Tm^{(j)}. \quad (26)$$

Substituting equation (26) into equation (23), one finds the directions of steepest ascent of the parametric functional $P^\alpha$:

$$l^{\alpha(i)} = F_T^{(i)*}(A^{(i)} m^{(i)} - d^{(i)}) + \alpha(c_1 l^{(i)} + c_2 l_{G_T}^{(i)}), \quad (27)$$

where $l^{(i)}$ are the directions of steepest ascent of the smoothing or focusing stabilizing functionals.

Adaptive regularization may be implemented to decrease the regularization parameter as the iterative process (22) proceeds until it is either terminated when the misfit reaches a desired level:

$$\varphi(m_{k+1}) = \|r_{k+1}\|_D^2 = \delta_d, \quad (28)$$

or a maximum number of predetermined iterations is reached, or the misfit fails to decrease by a predetermined threshold between iterations.

EXAMPLE 2

The following is a synthetic example of the simultaneous imaging different physical properties of an examined medium from the joint inversion of observed gravity and magnetic data (FIGS. 2a-2d).

The true density model 15 consists of a 400 m cube of 1 g/cm$^3$ anomalous density buried at 300 m depth beneath a 100 m thick layer of 0.5 g/cm$^3$ anomalous density in an otherwise homogeneous host. Synthetic gravity data were simulated for this model.

The true susceptibility model 16 consists of a 400 m cube of 0.1 (SI) susceptibility buried at 300 m depth in an otherwise homogeneous, nonmagnetic host. Synthetic magnetic data were simulated for this model.

The synthetic gravity and magnetic data were jointly inverted using a minimum norm stabilizer and Gramian constraints on the model parameters, with no other a priori information used. The density model recovered from joint inversion 17 and the susceptibility model recovered from joint inversion 18 recover model parameters similar to the true models.

EXAMPLE 3

The following is another synthetic example of the simultaneous imaging different physical properties of an examined medium from the joint inversion of observed gravity and magnetic data (FIGS. 3a-3d).

The true density model 19 consists of a 400 m cube of 0.1 g/cm$^3$ anomalous density buried at 300 m depth in an otherwise homogeneous host. Synthetic gravity data were simulated for this model.

The true susceptibility model 20 consists of a 400 m cube of 0.1 (SI) susceptibility buried at 300 m depth beneath a 100 m thick layer of 0.05 (SI) susceptibility in an otherwise homogeneous, nonmagnetic host. Synthetic magnetic data were simulated for this model.

The synthetic gravity and magnetic data were jointly inverted using a minimum norm stabilizer and Gramian constraints on the model parameters, with no other a priori information used. The density model recovered from joint inversion 21 and the susceptibility model recovered from joint inversion 22 recover model parameters similar to the true models.

Embodiments of the present invention may comprise or utilize a special purpose or general-purpose computer including computer hardware, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are physical non-transitory storage media. Computer-readable media that carry computer-executable instructions are transmission media. Thus, by way of example, and not limitation, embodiments of the invention can comprise at least two distinctly different kinds of computer-readable media: physical non-transitory storage media and transmission media.

Physical non-transitory storage media includes RAM, ROM, EEPROM, CD-ROM or other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to physical storage media (or vice versa). For example, computer-executable instructions or data structures received over a network or data link can be buffered in RAM within a network interface module (e.g., a "NIC"), and then eventually transferred to computer system RAM and/or to less volatile physical storage media at a computer system. Thus, it should be understood that physical storage media can be included in computer system components that also (or even primarily) utilize transmission media.

Computer-executable instructions comprise, for example, instructions and data which cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

The methods disclosed herein comprise one or more steps or actions for achieving the described method. The method steps and/or actions may be interchanged with one another without departing from the scope of the present invention. In other words, unless a specific order of steps or actions is required for proper operation of the embodiment, the order and/or use of specific steps and/or actions may be modified without departing from the scope of the present invention.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

What is claimed is:

1. A physical non-transitory computer readable medium having stored thereon computer executable instructions that when executed by a processor cause a computing system to perform a method for simultaneous imaging of different physical properties of an examined medium from a simultaneous joint inversion of multiple datasets of physical field/signal measurements, the method comprising:
    a. measuring with at least two sensors located in proximity to the examined medium at least one component of at least two physical fields and/or signals and recording by a corresponding recording device observed geophysical data generated as a response from the examined medium;
    b. constructing, based on the measured at least one component of the at least two different physical fields and/or signals, a Gramian space with a norm providing a measure of correlation between different model parameters and/or their transforms and/or their attributes that correspond to the at least two different physical fields and/or signals, the measure of correlation specifying a degree of similarity between a distribution of model parameters and/or their transforms and/or their attributes for a first one of the physical fields and/or signals and a distribution of model parameters and/or their transforms and/or their attributes for a second one of the physical fields and/or signals, wherein the Gramian space is a Hilbert space formed by integrable functions describing corresponding model parameters within a volume, V, of the examined medium with an inner product operation defined by a corresponding Gram matrix;
    c. determining a nonnegative Gramian functional equal to the determinant of the Gram matrix of at least two model parameters and/or their attributes;
    d. determining smoothing or focusing stabilizing functionals for producing smooth inverse images or images with sharp boundaries;
    e. determining predicted geophysical data based in part on the at least two model parameters and/or their attributes;
    f. constructing a parametric functional defined as a linear combination of misfit functionals for at least two observed geophysical data and predicted geophysical data, smoothing or focusing stabilizing functionals, and the Gramian functional, wherein the Gramian functional is a measure of the distance between the distributions of the different model parameters and/or their transforms and/or their attributes in the Gramian space, wherein a shorter distance between the distributions of the different model parameters and/or their transforms and/or their attributes in the Gramian space is more indicative of the different model parameters and/or their transforms and/or their attributes corresponding to a single physical object in the examined medium;
    g. minimizing the parametric functional with the Gramian functional, in order to enforce the correlations between the model parameters and/or their transforms and/or their attributes to thereby determine the different model parameters and/or their transforms and/or their attributes that have shorter distances between them;
    h. determining multi-modal model parameters, which correspond to the minimum of the parametric functional, by solving a minimization problem for the parametric functional using linear and/or nonlinear optimization methods;
i. outputting the multi-modal parameters;
j. evaluating the multi-modal parameters against termination criteria;
k. if the termination criteria are not satisfied, the output multi-modal parameters are updated model parameters used in determining new multi-modal parameters; and
l. if the termination criteria are satisfied, drilling a hole along a path through the examined medium based on the outputted multi-modal parameters.

2. The non-transitory computer readable medium of claim 1, wherein the at least two different physical fields and/or signals comprise seismic data, gravity data, magnetic data, and electromagnetic data, seismic compressional and/or shear velocity, density, magnetic susceptibility and/or magnetization, and resistivity and/or conductivity.

3. The non-transitory computer readable medium of claim 1, wherein a nonnegative Gram functional is equal to the determinant of the Gram matrix of at least two transformed model parameters and/or their attributes.

4. The non-transitory computer readable medium of claim 1, wherein a nonnegative Gram functional is equal to the determinant of the Gram matrix of the spatial gradients of the model parameters and/or their attributes.

5. The non-transitory computer readable medium of claim 1, wherein the at least two sensors comprise a plurality of sensors arranged in an array on the surface or within the examined medium.

6. The non-transitory computer readable medium of claim 5, wherein the plurality of sensors include:
seismic, electric, magnetic, gravity, acoustic, and temperature field sensors.

7. The non-transitory computer readable medium of claim 5, wherein the plurality of sensors include optical, electromagnetic, elastic, and radio waves signal sensors.

8. The non-transitory computer readable medium of claim 5, wherein the plurality of sensors include x-ray, magnetic resonance, ultrasound, electrical, and radionuclide sensors.

9. The non-transitory computer readable medium of claim 1, wherein the measured data are input to a processor, and the processor includes executable instructions to:
a. numerically calculate a nonnegative Gramian functional equal to the determinant of the Gram matrix of at least two model parameters and/or their attributes;
b. numerically calculate smoothing or focusing stabilizing functionals for producing smooth inverse images or the images with sharp boundaries;
c. numerically calculate a parametric functional defined as a linear combination of the misfit functionals for at least two datasets, smoothing or focusing stabilizing functional, and the Gramian functional introduced above; and
d. numerically determine the multi-modal model parameters, which correspond to the minimum of the parametric functional, by solving a minimization problem for the parametric functional using linear and/or nonlinear optimization methods.

10. The non-transitory computer readable medium of claim 9, wherein a nonnegative Gram functional is equal to:
the determinant of the Gram matrix of at least two transformed model parameters and/or their attributes, or
the determinant of the Gram matrix of the spatial gradients of the model parameters and/or their attributes.

11. A system for simultaneous imaging of different physical properties of an examined medium from a simultaneous joint inversion of multiple datasets of physical field/signal measurements comprising:
one or more sensors; and
a computing system, the computing system comprising:
a processor; and
one or more physical non-transitory computer readable media having computer executable instructions stored thereon that when executed by the processor, cause the computing system to perform the following:
measure with at least two sensors located in proximity to the examined medium at least one component of at least two physical fields and/or signals and record by a corresponding recording device observed geophysical data generated as a response from the examined medium;
construct, based on the measured at least one component of the at least two different physical fields and/or signals, a Gramian space with a norm providing a measure of correlation between different model parameters and/or their transforms and/or their attributes that correspond to the at least two different physical fields and/or signals, the measure of correlation specifying a degree of similarity between a distribution of model parameters and/or their transforms and/or their attributes for a first one of the physical fields and/or signals and a distribution of model parameters and/or their transforms and/or their attributes for a second one of the physical fields and/or signals, wherein the Gramian space is a Hilbert space formed by integrable functions describing corresponding model parameters within a volume, V, of the examined medium with an inner product operation defined by a corresponding Gram matrix;
determine in the Gramian space a nonnegative Gramian functional equal to the determinant of the Gram matrix of at least two model parameters and/or their attributes;
determine smoothing or focusing stabilizing functionals for producing smooth inverse images or images with sharp boundaries;
determine predicted geophysical data based in part on the at least two model parameters and/or their attributes;
construct a parametric functional defined as a linear combination of misfit functionals for at least two observed geophysical data and predicted geophysical data, smoothing or focusing stabilizing functionals, and the Gramian functional, wherein the Gramian functional is a measure of the distance between the distributions of the different model parameters and/or their transforms and/or their attributes in the Gramian space, wherein a shorter distance between the distributions of the different model parameters and/or their transforms and/or their attributes in the Gramian space is more indicative of the different model parameters and/or their transforms and/or their attributes corresponding to a single physical object in the examined medium;
minimize the parametric functional with the Gramian functional, in order to enforce the correlations between the model parameters and/or their transforms and/or their attributes to thereby determine the different model parameters and/or their transforms and/or their attributes that have shorter distances between them;

determine multi-modal model parameters, which correspond to the minimum of the parametric functional, by solving a minimization problem for the parametric functional using linear and/or non-linear optimization methods;

output the multi-modal parameters;

evaluate the multi-modal parameters against termination criteria;

if the termination criteria are not satisfied, the output multi-modal parameters are updated model parameters used in determining new multi-modal parameters; and if the termination criteria are satisfied, cause a drill to modify a path through the examined medium based on the outputted multi-modal parameters.

12. The system of claim 11, wherein a nonnegative Gram functional is equal to the determinant of the Gram matrix of at least two transformed model parameters and/or their attributes.

13. The system of claim 11, wherein a nonnegative Gram functional is equal to the determinant of the Gram matrix of the spatial gradients of the model parameters and/or their attributes.

14. The system of claim 11, wherein the one or more sensors comprise a plurality of sensors arranged in an array on a surface of the examined medium or within the examined medium.

15. The system of claim 11, wherein the one or more sensors comprise seismic, electric, magnetic, gravity, acoustic, or temperature field sensors.

16. The system of claim 11, wherein the one or more sensors comprise optical, electromagnetic, elastic, radio wave, x-ray, magnetic resonance, ultrasound, electrical, or radionuclide sensors.

17. The system of claim 11, wherein the measured data are input into the processor of the computing system, and the processor includes executable instructions to:
 a. numerically calculate a nonnegative Gramian functional equal to the determinant of the Gram matrix of at least two model parameters and/or their attributes;
 b. numerically calculate smoothing or focusing stabilizing functionals for producing smooth inverse images or the images with sharp boundaries;
 c. numerically calculate a parametric functional defined as a linear combination of the misfit functionals for at least two datasets, smoothing or focusing stabilizing functional, and the Gramian functional introduced above; and
 d. numerically determine the multi-modal model parameters, which correspond to the minimum of the parametric functional, by solving a minimization problem for the parametric functional using linear and/or non-linear optimization methods.

18. The system of claim 17, wherein a nonnegative Gram functional is equal to the determinant of the Gram matrix of at least two transformed model parameters and/or their attributes.

19. The system of claim 17, wherein a nonnegative Gram functional is equal to the determinant of the Gram matrix of the spatial gradients of the model parameters and/or their attributes.

20. A system comprising:
 a drilling apparatus;
 a plurality of sensors;
 at least one processor; and
 a non-transitory computer readable medium storing instructions thereon that, when executed by the at least one processor, cause a computing system to:
  receive sensor data comprising a plurality of physical signals generated by an examined medium and recorded by the plurality of sensors positioned in proximity to the examined medium, the plurality of physical signals comprising a first physical signal and a second physical signal;
  generate, based on the received sensor data, a Gramian space indicating a measure of correlation between model parameters and associated attributes that correspond to the plurality of physical signals, wherein the measure of correlation indicates a degree of similarity between a first distribution of model parameters and the attributes for the first physical signal and a second distribution of model parameters and the attributes for the second physical signal;
  determine a non-negative Gramian functional based on a determinant of the Gramian space, the Gramian functional comprising a measure of distance between the distribution of model parameters and the second distribution of model parameters, the measure of distance comprising a measure of similarity in physical properties of the examined medium at different locations between physical signals detected by the plurality of sensors at the different locations;
  determine a stabilizing functional for producing smooth inverse images or images with sharp boundaries;
  determine predicted geophysical data based on the model parameters and associated attributes;
  generate a parametric functional including a linear combination of misfit functionals for two or more of the determined non-negative Gramian functional, stabilized function, and predicted geophysical data;
  minimize the parametric functional with the Gramian functional to enforce correlations between the model parameters and associated attributes;
  determine multi-modal model parameters corresponding to a minimization of the parametric functional; and
  cause the drilling apparatus to drill a hole along a path through the examined medium based on the determined multi-modal model parameters corresponding to the minimization of the parametric functional.

* * * * *